United States Patent [19]

Mikulski et al.

[11] Patent Number: 5,529,775
[45] Date of Patent: Jun. 25, 1996

[54] COMPOSITIONS COMPRISING ONCONASE(TM) AND CISPLATIN, MELPHALAN, OR DOXORUBICIN HCL

[75] Inventors: Stanislaw M. Mikulski, Essex Fells, N.J.; Wojciech J. Ardelt, New City, N.Y.

[73] Assignee: Alfacell Corporation, Bloomfield, N.J.

[21] Appl. No.: 283,971

[22] Filed: Aug. 1, 1994

Related U.S. Application Data

[63] Continuation of Ser. No. 921,180, Jul. 30, 1992, abandoned, which is a continuation-in-part of Ser. No. 436,141, Nov. 13, 1989, abandoned, which is a continuation-in-part of Ser. No. 178,118, Apr. 6, 1988, Pat. No. 4,882,421.

[51] Int. Cl.⁶ .............................. A61K 38/43; C12N 9/22
[52] U.S. Cl. ..................... 424/94.6; 435/199; 530/350; 514/12
[58] Field of Search ................ 530/350; 424/94.6; 435/199; 514/12

[56] References Cited

U.S. PATENT DOCUMENTS 4,882,421  11/1989  Shogen et al. ................... 530/350
4,888,172  12/1989  Szebenyi et al. ................. 424/105
5,175,005  12/1992  Fukushima et al. .............. 424/583

OTHER PUBLICATIONS

Abstract (Dialog file 155 Accession No. 89146182) Legha, S. S. 1989, Semin Oncol. 16: 34–44.

Hird et al. 1990. Gener and Cancer, (P. Carney et al. eds.) John Wiley & Sons Ltd., N.Y.. pp. 184–189.

Ardelt et al. 1991. J. Biol. Chem. 266(1):245–251.

Mikulski et al. 1990. Cell Tissue Kinet. 23:237–246.

Primary Examiner—Robert A. Wax
Assistant Examiner—K. Cochrane Carlson

[57] ABSTRACT

A pharmaceutical known by the trademark ONCONASE, as described in pending commonly owned application application Ser. No. 07/436,141 filed Nov. 13, 1989, is combined with drugs sold under the names cisplatin, Melphalan and Doxorubicin HCl. The combinations of ONCONASE with these drugs has unexpected bioactivity in vitro against OVCAR-3 human ovarian adenocarcinoma cells.

3 Claims, No Drawings

COMPOSITIONS COMPRISING ONCONASE(™) AND CISPLATIN, MELPHALAN, OR DOXORUBICIN HCL

This application is a continuation of application Ser. No. 07/921,180, filed Jul. 30, 1992, now abandoned, which is a continuation-in-part of application Ser. No. 07/436,141, filed Nov. 13, 1989, now abandoned, which is a continuation-in-part of application Ser. No. 07/178,118, filed Apr. 6, 1988, now U.S. Pat. No. 4,882,421.

BACKGROUND OF THE INVENTION

The invention relates to pharmaceuticals, and more particularly relates to pharmaceuticals for use in treating cells which cause cancer tumor in humans.

The above-referenced patent application discloses a pharmaceutical which will be referred to herein by the trademark ONCONASE. It has not been determined that when this pharmaceutical is used in vitro in a combined therapy with three other drugs, the results of the combined therapy are, in certain instances, much more bioactive than would be expected.

These other drugs are known as Cisplatin, Melphalan and ADRIAMYCIN.

DETAILED DESCRIPTION OF PREFERRED EMBODIMENTS

In vitro data indicate that a combination of ONCONASE with a drug sold under the name Cisplatin is much more bioactive against human ovarian OVCAR-3 adenocarcinoma than would be expected, given the separate activities of ONCONASE and Cisplatin. In vitro also data indicate that a combination of ONCONASE with a drug sold under the name Melphalan is much more bioactive against human ovarian OVCAR-3 adenocarcinoma than would be expected, given the separate activities of ONCONASE and Melphalan. In vitro data indicate that a combination of ONCONASE with a drug sold under the trademark ADRIAMYCIN is much more bioactive against human ovarian OVCAR-3 adenocarcinoma than would be expected given the separate activities of ONCONASE and ADRIAMYCIN.

The preferred embodiment of the invention was tested using a cell culture assay. In such an assay, a cell line of known growth rate over a predetermined period is treated with the substance under test and the growth of the treated cells is compared with the growth which would ordinarily be expected from untreated cells.

ONCONASE, described in the above-referenced pending patent application and manufactured in accordance with the methodology described in U.S. Pat. No. 4,882,421 (which methodology is hereby incorporated herein by reference as if fully set forth herein) was dissolved in phosphate buffered saline (PBS) to obtain 1 mg/ml stock solution.

Cisplatin, also known as cis-diamminedichloroplatinum, is a heavy metal complex containing a central atom of platinum surrounded by two chloride atoms and two ammonia molecules in the cis position. It has the molecular formula Pt $Cl_2H_6N_2$ and a molecular weight of 300.1.

Melphalan, also known as L-phenylalanine mustard, phenylalanine mustard, L-PAM, or L-sarcolysin, is 4-[bis(2-chloroethyl)amino]-L-phenylalanine.

ADRIAMYCIN is a trademark for Doxorubicin HCl, USP. Doxorubicin is an anthracycline antibiotic isolated from cultures of *Streptomyces peucetius* var. caesius. Doxorubicin consists of a napthacenequinone nucleus linked through a glycosidic bond at ring atom 7 to an amino sugar, daunosamine.

The assay system utilized the OVCAR-3 human ovarian adenocarcinoma cell line, obtained from the American Type Culture Collection (accession number ATCC HTB 161). The cell line was cultured in RPMI 1640 medium and supplemented with 20% heat-inactivated fetal bovine serum, 200 mM L-glutamine, 10,000 units per 1 ml penicillin, 10 mg per 1 ml streptomycin, 25 µg per 1 ml fungizone, 10 mM HEPES buffer and 10 µg per 1 ml bovine insulin. This was the complete growth medium.

The cells were seeded into 96-well tissue culture plates at a density of 6000 viable cells (50 µl ) per well. The cells were allowed to settle for 24 hours and then 50 µl of appropriate ONCONASE and/or Cisplatin, Melphalan or ADRIAMYCIN solutions were added per well. The following final concentrations were used:

a) ONCONASE, 20 ng to 10 µg/ml;

b) Cisplatin, 10 to 500 nM;

c) Melphalan, 0.25 to 5 µM; and d) ADRIAMYCIN, 5 to 100 nM.

The plates were incubated for an additional six days at 37° C. and 5% carbon dioxide atmosphere. The total assay time was consequently seven days (one day in which the cells are allowed to settle, and six days of incubation). Percentages of viable cells were then determined using the MTT colorimetric assay using the Bio-Rad EIA microtiter plate reader.

The number of cells was determined by a direct count in an AO-Spencer "Brightline" hemocytometer with a Neubauer ruling. Attached cells were washed three times with Hanks' Balanced Salt Solution and treated with 2 ml of a 0.25% Trypsin—0.02% EDTA solution in buffered saline for about thirty seconds. The solution was removed and the cells were left at 37° C. for 10 minutes, then suspended in 10 ml of the complete growth medium. The 0.25 ml of the cell suspension was diluted with 0.75 ml of the complete growth medium and then 1 ml of 0.5% Trypan Blue solution was added and viable cells were counted.

Tables 1, 2 and 3 present the result of the above experiments. Except for the $ED_{50}$ values, these tables are expressed in the Interaction Index developed by Berenbaum. In this Interaction Index, a result of 1.0 indicates that the two drugs do not interact, i.e. that their combined effectiveness against a particular cell line is unchanged from what would be expected from using them individually. An Interaction Index result which is greater than 1.0 indicates that the two drugs are antagonistic, i.e. that their combined effectiveness against a particular cell line is less than what would be expected from using them individually. Progressively higher Interaction Index results indicate progressively greater antagonism. An Interaction Index result which is less than 1.0 indicates that the two drugs are synergistic, i.e. that their combined effectiveness against a particular cell line is greater than what would be expected from using them individually. As the Interaction Index approaches 0 (maximum synergism), this indicates progressively greater synergism. Thus, a lower number indicates a higher bioactivity against the cell line used in the experiment. The $ED_{50}$ values represent isoeffective doses; they indicate the dose required to halve the growth rate of the cells undergoing the assay. Thus, the lower the $ED_{50}$ figure, the smaller the dose required to achieve the same bioactivity.

TABLE 1

Interaction Index and $ED_{50}$ Values for varying doses of ONCONASE together with Cisplatin for OVCAR-3 human ovarian adenocarcinoma cells and $ED_{50}$ values for ONCONASE and Cisplatin individually

| ONCONASE Dose (μg/ml) | 0 | 0.02 | 0.2 | 2.0 | $ED_{50}$ |
|---|---|---|---|---|---|
| ONCONASE Alone | | | | | 1.447 |
| ONCONASE + 10 mM Cisplatin | | 1.159 | 0.891 | 0.482 | 0.697 |
| ONCONASE + 25 mM Cisplatin | | 1.098 | 0.830 | 0.421 | 0.609 |
| ONCONASE + 50 mM Cisplatin | | 1.132 | 0.864 | 0.455 | 0.658 |
| ONCONASE + 100 mM Cisplatin | | 0.858 | 0.590 | 0.181 | 0.262 |
| ONCONASE + 250 mM Cisplatin | | 0.700 | 0.432 | 0.023 | 0.034 |
| ONCONASE + 500 mM Cisplatin | | 0.685 | 0.417 | 0.008 | 0.011 |
| $ED_{50}$ Values*: | 316.509 | 214.299 | 129.616 | <0.001 | |

*for Cisplatin in combination with respective concentrations of ONCONASE (vertically); $ED_{50}$ value for Cisplatin at 0 μl ONCONASE is for Cisplatin alone, OVCAR-3 cells being considered resistant to Cisplatin alone

TABLE 2

Interaction Index and $ED_{50}$ Values for varying doses of ONCONASE together with Melphalan for OVCAR-3 human ovarian adenocarcinoma cells and $ED_{50}$ values for ONCONASE and Melphalan individually

| ONCONASE Dose (μg/ml) | 0 | 0.02 | 0.2 | 2.0 | $ED_{50}$ |
|---|---|---|---|---|---|
| ONCONASE Alone | | | | | |
| ONCONASE + 0.25 μM Melphalan | | 1.701 | 1.492 | 0.747 | 1.705 |
| ONCONASE + 0.5 μM Melphalan | | 1.778 | 1.569 | 0.824 | 1.881 |
| ONCONASE + 0.75 μM Melphalan | | 1.746 | 1.537 | 0.792 | 1.808 |
| ONCONASE + 1.0 μM Melphalan | | 1.142 | 0.934 | 0.189 | 0.411 |
| ONCONASE + 2.5 μM Melphalan | | 0.987 | 0.779 | 0.034 | 0.051 |
| ONCONASE + 5.0 μM Melphalan | | 0.975 | 0.766 | 0.021 | 0.022 |
| $ED_{50}$ Values*: | 4.786 | 4.623 | 3.624 | 0.056 | |

*for Melphalan in combination with respective concentrations of ONCONASE (vertically); $ED_{50}$ value for Melphalan at 0 μl ONCONASE is for Melphalan alone, OVCAR-3 cells being considered resistant to Melphalan alone

TABLE 3

Interaction Index and $ED_{50}$ Values for varying doses of ONCONASE together with ADRIAMYCIN for OVCAR-3 human ovarian adenocarcinoma cells and $ED_{50}$ values for ONCONASE and ADRIAMYCIN individually

| ONCONASE Dose (μg/ml) | 0 | 0.02 | 0.2 | 2.0 | $ED_{50}$ |
|---|---|---|---|---|---|
| ONCONASE Alone | | | | | 1.166 |
| ONCONASE + 5 nM ADRIAMYCIN | | 1.744 | 1.305 | 0.881 | 0.957 |
| ONCONASE + 10 nM ADRIAMYCIN | | 1.702 | 1.263 | 0.839 | 0.908 |
| ONCONASE + 25 nM ADRIAMYCIN | | 1.208 | 0.769 | 0.346 | 0.332 |
| ONCONASE + 50 nM ADRIAMYCIN | | 0.923 | 0.484 | 0.061 | 0.001 |
| $ED_{50}$ Values*: | 37.340 | 34.473 | 18.090 | 2.265 | |

TABLE 3-continued

Interaction Index and $ED_{50}$ Values for varying doses of ONCONASE together with ADRIAMYCIN for OVCAR-3 human ovarian adenocarcinoma cells and $ED_{50}$ values for ONCONASE and ADRIAMYCIN individually

| ONCONASE Dose (μg/ml) | 0 | 0.02 | 0.2 | 2.0 | $ED_{50}$ |
|---|---|---|---|---|---|

*for ADRIAMYCIN in combination with respective concentrations of ONCONASE (vertically); $ED_{50}$ value for Adriamycin at 0 μl ONCONASE is for ADRIAMYCIN alone, OVCAR-3 cells being considered resistant to ADRIAMYCIN alone These results demonstrate that, in the instances shown, the bioactivities of ONCONASE combined with Cisplatin, Melphalan and ADRIAMYCIN on OVCAR-3 human ovarian adenocarcinoma are much greater than would be expected from the bioactivities of the individual drugs alone. (Indeed, the OVCAR-3 cell line originated from a patient who was clinically resistant to Cisplatin, Melphalan and ADRIAMYCIN.) This may be seen from the $ED_{50}$ figures which are along the right edge of the Tables. These figures represent computed isoeffective doses; the figure shown is the amount of material which would be required to halve the growth rate of the cells undergoing the assay. Thus, the lower the $ED_{50}$ figure, the smaller the dose required to achieve the same bioactivity.

Chemical Analysis and Composition of ONCONASE

ONCONASE has been well characterized chemically. While ONCONASE is a protein isolated from Rana pipiens, it is believed that ONCONASE may be produced using genetic engineering techniques, as long as the end result has the following chemistry and structure:

ONCONASE is a pure protein (i.e. homogeneous, as established by standard tests which are used to assay the homogeneity of proteins). By electrophoresis, the molecular weight of ONCONASE is approximately 14,500 Daltons. Calculation of the molecular weight based upon the below listed amino acid sequence indicates that the molecular weight should be 11,819 Daltons. However, because metal ions may have bonded to the protein despite all efforts to remove them, and because different isotopes may be involved, the molecular weight of ONCONASE as determined by mass spectroscopy is 12,430 Daltons. In view of this discrepancy, the molecular weight of ONCONASE as determined by mass spectrometry will be considered to be approximately 12,000 Daltons. ONCONASE has an isoelectric point pI which is at least 9.5 and may be as high as 10.5. ONCONASE has a blocked amino terminal group and is essentially free of carbohydrates (as determined by anthrone and orcinol methods). ONCONASE has the following amino acid composition:

Amino Acid Analysis

| AMINO ACID RESIDUE | MOL % (24 HOUR ACID HYDROLYSIS) |
|---|---|
| Aspartic acid/Aspargine | 13.39 |
| Threonine | 9.84 (Note 1) |
| Serine | 8.08 (Note 1) |
| Glutamic acid/Glutamine | 5.88 |
| Proline | 3.98 |
| Glycine | 2.98 |
| Alanine | 2.92 |

-continued

Amino Acid Analysis

| AMINO ACID RESIDUE | MOL % (24 HOUR ACID HYDROLYSIS) |
|---|---|
| Cystine/2 | 7.77 |
| Valine | 7.77 |
| Methionine | 0.94 |
| Isoleucine | 5.29 (Note 2) |
| Leucine | 4.95 |
| Tyrosine | 2.85 |
| Phenylalanine | 5.73 |
| Histidine | 2.99 |
| Lysine | 11.78 |
| Arginine | 2.85 |
| Tryptophan | Not Determined (Note 3) |
| Approximate Total | 99.99% |

Note 1: Threonine and serine are partially destroyed during hydrolysis and this value is corrected for such partial destruction.
Note 2: This value is corrfected for incomplete hydrolysis.
Note 3: Tryptophan cannot be detected in acid hydrolysis of proteins becase it is destroyed and is consequently shown as Not Determined. However, analysis of the ultraviolet spectrum revealed the presence of one tryptophan residue per molecule.

Amino Acid Composition
(as calculated from amino acid sequence)

| AMINO ACID | NUMBER OF RESIDUES PER MOLECULE OF MATERIAL |
|---|---|
| Aspartic acid | 6 |
| Asparagine | 8 |
| Threonine | 10 |
| Serine | 8 |
| Glutamic acid | 3 |
| Pyroglutamic acid | 1 |
| Glutamine | 2 |
| Proline | 4 |
| Glycine | 3 |
| Alanine | 3 |
| Cystine/2 | 8 |
| Valine | 8 |
| Methionine | 1 |
| Isoleucine | 6 |
| Leucine | 5 |
| Tyrosine | 3 |
| Phenylalanine | 6 |
| Histidine | 3 |
| Lysine | 12 |
| Arginine | 3 |
| Tryptophan | 1 |
| Approximate Total | 104 |

ONCONASE has been sequenced. As is shown below, the total length of the sequence is 104 residues. The N-terminus of the protein is pyroglutamic acid (<Glu). This is a cyclized derivative of glutamic acid which is devoid of the free amino group necessary for direct sequencing and which therefore "blocks" the N-terminus of the protein.

When the shorter fragment described in U.S. Pat. No. 4,882,421 was cleaved with pyroglutamate aminopeptidase, pyroglutamic acid was removed from the shorter fragment, permitting sequencing to commence at the second residue. Such cleavage is a strong indication that the N-terminus is pyroglutamic acid since pyroglutamate aminopeptidase only cleaves pyroglutamic acid. The presence of pyroglutamic acid was further confirmed by mass spectrometry of the referenced shorter fragment. The molecular weight of this shorter fragment determined by mass spectrometry agreed well with the weight as calculated assuming that pyroglutamic acid was present and disagreed with the weight as calculated assuming that glutamic acid was present.

ONCONASE has the following amino acid sequence:

```
 1    2    3    4    5    6    7    8    9   10
<Glu—Asp—Trp—Leu—Thr—Phe—Gln—Lys—Lys—His—

11                                           20
Ile—Thr—Asn—Thr—Arg—Asp—Val—Asp—Cys—Asp—

21                                           30
Asn—Ile—Met—Ser—Thr—Asn—Leu—Phe—His—Cys—

31                                           40
Lys—Asp—Lys—Asn—Thr—Phe—Ile—Tyr—Ser—Arg—

41                                           50
Pro—Glu—Pro—Val—Lys—Ala—Ile—Cys—Lys—Gly—

51                                           60
Ile—Ile—Ala—Ser—Lys—Asn—Val—Leu—Thr—Thr—

61                                           70
Ser—Glu—Phe—Tyr—Leu—Ser—Asp—Cys—Asn—Val—

71                                           80
Thr—Ser—Arg—Pro—Cys—Lys—Tyr—Lys—Leu—Lys—

81                                           90
Lys—Ser—Thr—Asn—Lys—Phe—Cys—Val—Thr—Cys—

91                                          100
Glu—Asn—Gln—Ala—Pro—Val—His—Phe—Val—Gly—

101            104
Val—Gly—Ser—Cys
```

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 104 amino acids
( B ) TYPE: amino acid
( C ) STRANDEDNESS: single
( D ) TOPOLOGY: linear ( i i ) MOLECULE TYPE: protein (iii) HYPOTHETICAL: N (iv) ANTI-SENSE: N (v) FRAGMENT TYPE: N-terminal (vi) ORIGINAL SOURCE:
  (A) ORGANISM: Rana pipiens
  (D) DEVELOPMENTAL STAGE: Embryo (xi) SEQUENCE DESCRIPTION: SEQ ID NO:1:

| Glu | Asp | Trp | Leu | Thr | Phe | Gln | Lys | Lys | His | Ile | Thr | Asn | Thr | Arg | Asp |
|---|---|---|---|---|---|---|---|---|---|---|---|---|---|---|---|
| 1 | | | | 5 | | | | | 10 | | | | | 15 | |
| Val | Asp | Cys | Asp | Asn | Ile | Met | Ser | Thr | Asn | Leu | Phe | His | Cys | Lys | Asp |
| | | | 20 | | | | | 25 | | | | | 30 | | |
| Lys | Asn | Thr | Phe | Ile | Tyr | Ser | Arg | Pro | Glu | Pro | Val | Lys | Ala | Ile | Cys |
| | | 35 | | | | | 40 | | | | | 45 | | | |
| Lys | Gly | Ile | Ile | Ala | Ser | Lys | Asn | Val | Leu | Thr | Thr | Ser | Glu | Phe | Tyr |
| | 50 | | | | | 55 | | | | | 60 | | | | |
| Leu | Ser | Asp | Cys | Asn | Val | Thr | Ser | Arg | Pro | Cys | Lys | Tyr | Lys | Leu | Lys |
| 65 | | | | | 70 | | | | | 75 | | | | | 80 |
| Lys | Ser | Thr | Asn | Lys | Phe | Cys | Val | Thr | Cys | Glu | Asn | Gln | Ala | Pro | Val |
| | | | | 85 | | | | | 90 | | | | | 95 | |
| His | Phe | Val | Gly | Val | Gly | Ser | Cys | | | | | | | | |
| | | | 100 | | | | | | | | | | | | |

Although a preferred embodiment has been described above, the scope of the invention is limited only by the following claims:

We claim:

1. A bioactive pharmaceutical comprising a protein having the following amino acid sequence:

```
 1   2   3   4   5   6   7   8   9   10
<Glu—Asp—Trp—Leu—Thr—Phe—Gln—Lys—Lys—His—

11                                        20
Ile—Thr—Asn—Thr—Arg—Asp—Val—Asp—Cys—Asp—

21                                        30
Asn—Ile—Met—Ser—Thr—Asn—Leu—Phe—His—Cys—

31                                        40
Lys—Asp—Lys—Asn—Thr—Phe—Ile—Tyr—Ser—Arg—

41                                        50
Pro—Glu—Pro—Val—Lys—Ala—Ile—Cys—Lys—Gly—

51                                        60
Ile—Ile—Ala—Ser—Lys—Asn—Val—Leu—Thr—Thr—

61                                        70
Ser—Glu—Phe—Tyr—Leu—Ser—Asp—Cys—Asn—Val—

71                                        80
Thr—Ser—Arg—Pro—Cys—Lys—Tyr—Lys—Leu—Lys—

81                                        90
Lys—Ser—Thr—Asn—Lys—Phe—Cys—Val—Thr—Cys—

91                                        100
Glu—Asn—Gln—Ala—Pro—Val—His—Phe—Val—Gly—

101        104
Val—Gly—Ser—Cys
``` and Cisplatin.

2. A bioactive pharmaceutical comprising a protein having the following amino acid sequence:

```
 1   2   3   4   5   6   7   8   9   10
<Glu—Asp—Trp—Leu—Thr—Phe—Gln—Lys—Lys—His—

11                                        20
Ile—Thr—Asn—Thr—Arg—Asp—Val—Asp—Cys—Asp—

21                                        30
Asn—Ile—Met—Ser—Thr—Asn—Leu—Phe—His—Cys—

31                                        40
Lys—Asp—Lys—Asn—Thr—Phe—Ile—Tyr—Ser—Arg—

41                                        50
Pro—Glu—Pro—Val—Lys—Ala—Ile—Cys—Lys—Gly—

51                                        60
Ile—Ile—Ala—Ser—Lys—Asn—Val—Leu—Thr—Thr—

61                                        70
Ser—Glu—Phe—Tyr—Leu—Ser—Asp—Cys—Asn—Val—

71                                        80
Thr—Ser—Arg—Pro—Cys—Lys—Tyr—Lys—Leu—Lys—

81                                        90
Lys—Ser—Thr—Asn—Lys—Phe—Cys—Val—Thr—Cys—

91                                        100
Glu—Asn—Gln—Ala—Pro—Val—His—Phe—Val—Gly—

101        104
Val—Gly—Ser—Cys
``` and 4-[bis (2-chloroethyl) amino]-L-phenylalanine.

3. A bioactive pharmaceutical comprising a protein having the following amino acid sequence:

```
 1   2   3   4   5   6   7   8   9   10
<Glu—Asp—Trp—Leu—Thr—Phe—Gln—Lys—Lys—His—

11                                        20
Ile—Thr—Asn—Thr—Arg—Asp—Val—Asp—Cys—Asp—
```

21                                      30
Asn—Ile—Met—Ser—Thr—Asn—Leu—Phe—His—Cys—

31                                      40
Lys—Asp—Lys—Asn—Thr—Phe—Ile—Tyr—Ser—Arg—

41                                      50
Pro—Glu—Pro—Val—Lys—Ala—Ile—Cys—Lys—Gly—

51                                      60
Ile—Ile—Ala—Ser—Lys—Asn—Val—Leu—Thr—Thr—

61                                      70
Ser—Glu—Phe—Tyr—Leu—Ser—Asp—Cys—Asn—Val—

71                                      80
Thr—Ser—Arg—Pro—Cys—Lys—Tyr—Lys—Leu—Lys—

81                                      90
Lys—Ser—Thr—Asn—Lys—Phe—Cys—Val—Thr—Cys—

91                                      100
Glu—Asn—Gln—Ala—Pro—Val—His—Phe—Val—Gly—

101      104
Val—Gly—Ser—Cys and Doxorubicin HCl, USP.

* * * * *